US010421234B2

(12) United States Patent
Ju

(10) Patent No.: US 10,421,234 B2
(45) Date of Patent: Sep. 24, 2019

(54) METHOD FOR MANUFACTURING RADIATION INTENSITY MODULATING BODY AND DEVICE FOR MANUFACTURING SAME

(71) Applicant: Samsung Life Public Welfare Foundation, Seoul (KR)

(72) Inventor: Sang Gyu Ju, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 133 days.

(21) Appl. No.: 15/534,706

(22) PCT Filed: Dec. 16, 2015

(86) PCT No.: PCT/KR2015/013776
§ 371 (c)(1),
(2) Date: Jun. 9, 2017

(87) PCT Pub. No.: WO2016/099142
PCT Pub. Date: Jun. 23, 2016

(65) Prior Publication Data
US 2017/0361535 A1    Dec. 21, 2017

(30) Foreign Application Priority Data

Dec. 16, 2014  (KR) .................. 10-2014-0181629

(51) Int. Cl.
*G06F 19/00* (2018.01)
*B29C 64/393* (2017.01)
(Continued)

(52) U.S. Cl.
CPC .......... *B29C 64/393* (2017.08); *A61N 5/1038* (2013.01); *A61N 5/1043* (2013.01);
(Continued)

(58) Field of Classification Search
CPC .... A61N 2005/1095; A61N 2005/1096; A61N 5/1038; A61N 5/1043; A61N 5/1065;
(Continued)

(56) References Cited

U.S. PATENT DOCUMENTS

2005/0254622 A1* 11/2005 Llacer ................. A61N 5/1031
378/65
2006/0097204 A1* 5/2006 Yanagisawa ........ A61N 5/1042
250/505.1

(Continued)

FOREIGN PATENT DOCUMENTS

EP       2 116 278 A1   11/2009
KR   10-2010-0119109 A  11/2010
(Continued)

OTHER PUBLICATIONS

International Search Report and Written Opinion issued by the Korean Intellectual Property Office, acting as the ISA, for International Application PCT/KR2015/013776 dated Mar. 14, 2016.

*Primary Examiner* — Kidest Bahta
(74) *Attorney, Agent, or Firm* — McCarter & English, LLP

(57) ABSTRACT

Provided are a method and apparatus for manufacturing a radiation beam intensity modulator. The method includes: obtaining dose modulation information expressed as a density matrix or three-dimensional (3D) structure information provided from a radiotherapy treatment planning system; obtaining design condition information of a radiation beam intensity modulator provided from the radiotherapy treatment planning system; generating a radiation beam intensity modulator structure based on the design condition information of the radiation beam intensity modulator and the dose modulation information expressed as the density matrix or the 3D structure information; adjusting the radiation beam intensity modulator structure by comparing at least one of an (Continued)

actual manufacturing condition and a treatment condition with the design condition information of the radiation beam intensity modulator; and manufacturing the radiation beam intensity modulator based on the radiation beam intensity modulator structure that is adjusted.

14 Claims, 16 Drawing Sheets

(51) Int. Cl.
    *B29C 64/20*     (2017.01)
    *A61N 5/10*     (2006.01)
    *B33Y 80/00*     (2015.01)
    *B33Y 10/00*     (2015.01)

(52) U.S. Cl.
    CPC ......... *A61N 5/1065* (2013.01); *A61N 5/1077* (2013.01); *B29C 64/20* (2017.08); *B33Y 10/00* (2014.12); *B33Y 80/00* (2014.12); *A61N 2005/1095* (2013.01); *A61N 2005/1096* (2013.01)

(58) Field of Classification Search
    CPC .... A61N 5/1077; B29C 64/20; B29C 64/393; B33Y 10/00; B33Y 80/00
    See application file for complete search history.

(56) References Cited

U.S. PATENT DOCUMENTS

| | | | |
|---|---|---|---|
| 2008/0067401 A1* | 3/2008 | Harada | A61N 5/10 250/396 R |
| 2008/0260098 A1* | 10/2008 | Al-Sadah | A61N 5/1042 378/65 |
| 2010/0034357 A1* | 2/2010 | Svesson | A61N 5/1042 378/152 |
| 2011/0301449 A1* | 12/2011 | Maurer, Jr. | A61B 6/032 600/411 |
| 2012/0001096 A1* | 1/2012 | Keppel | A61N 5/1031 250/492.3 |
| 2012/0119105 A1* | 5/2012 | Iwata | G21K 1/10 250/396 ML |
| 2015/0006098 A1 | 1/2015 | Ju | |

FOREIGN PATENT DOCUMENTS

| | | |
|---|---|---|
| KR | 10-2011-0039514 A | 4/2011 |
| KR | 10-2012-0079726 A | 7/2012 |
| KR | 10-2012-0087862 A | 8/2012 |
| KR | 10-1437268 B1 | 9/2014 |
| WO | WO 2012/081743 A1 | 6/2012 |

\* cited by examiner

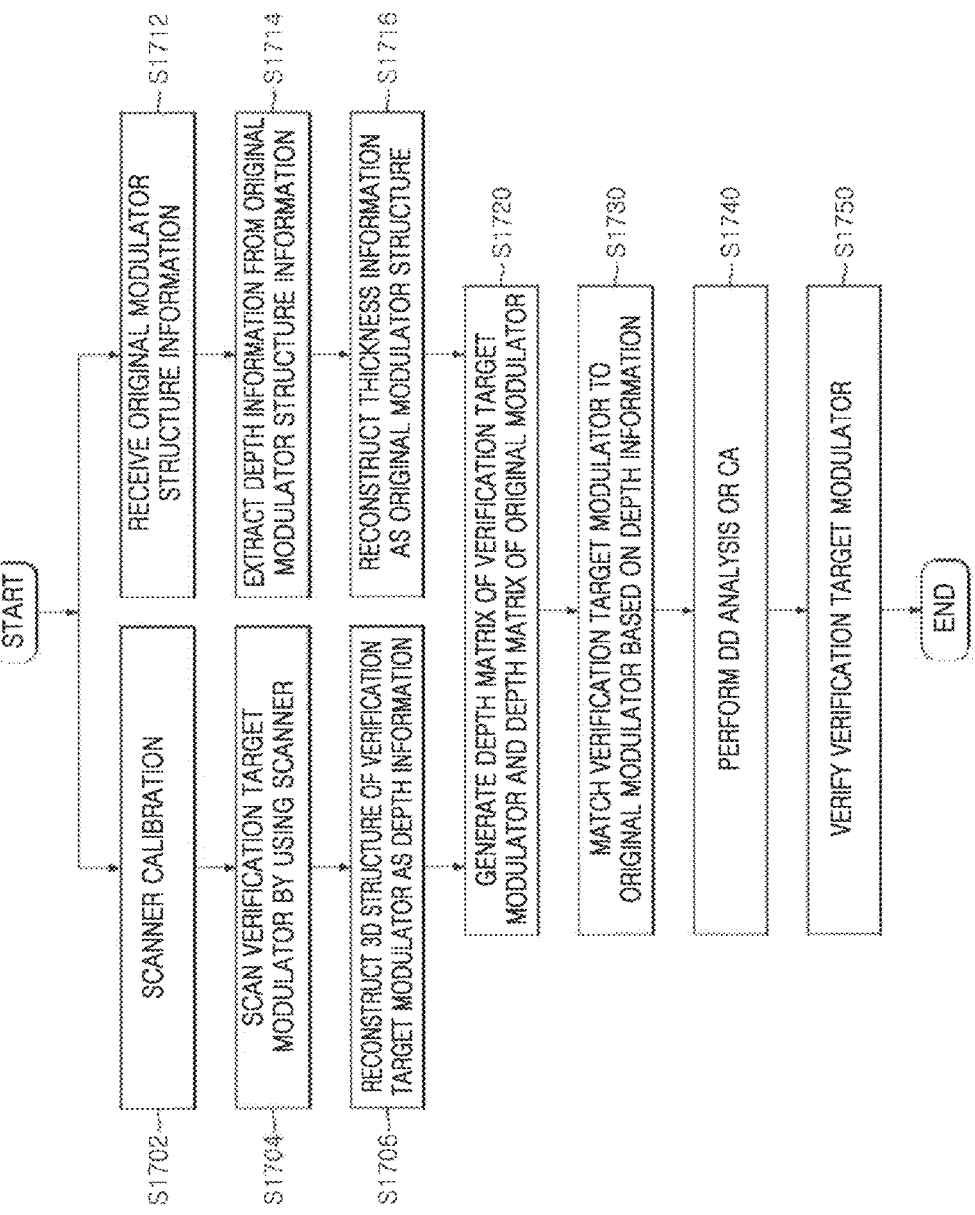

METHOD FOR MANUFACTURING RADIATION INTENSITY MODULATING BODY AND DEVICE FOR MANUFACTURING SAME

CROSS-REFERENCE TO RELATED APPLICATIONS

This application is the National Stage entry under 35 U.S.C. § 371 of International Application Number PCT/KR2015/013776 filed on Dec. 16, 2015, published on Jun. 23, 2016 under publication number WO 2016/099142 A1, which claims the benefit of priority under 35 U.S.C. § 119 of Korean patent application number 10-2014-0181629 filed Dec. 16, 2014.

TECHNICAL FIELD

The present invention relates to a method and apparatus for manufacturing a radiation beam intensity modulator, and more particularly, to a method and apparatus for manufacturing a radiation beam intensity modulator rapidly and precisely by using a three-dimensional (3D) printer.

BACKGROUND ART

In general, a radiation beam intensity modulator is a device for modulating a dose distribution of a radiation beam by being placed in a center of radiation beam or in contact with or inserted into a body of a patient.

A radiation beam intensity modulator is used to increase a tumor radiation dose and to protect surrounding normal tissues by modulating an intensity of a radiation beam in radiotherapy. The radiation beam intensity modulator is used for electron beam, X-ray, proton, and particle beam radiotherapies, and in particular, the radiation beam intensity modulator is essential in order to obtain a radiation dose distribution suitable for the shape of a tumor, in a case of the proton and particle beam radiotherapy.

In addition, the radiation beam intensity modulator is used to improve quality of an image through an enhanced beam quality when an image is obtained using radiation, because it is effective in irradiating a radiation beam to a desired region by adjusting an intensity of a specific region or blocking the radiation.

Recently, proton and particle beam radiotherapy facilities have been rapidly increased worldwide, and since the National Health Insurance has started to cover intensity modulated radiotherapy in Korea, a technique for intensity modulated through simple processes has been necessary.

However, according to a conventional intensity modulated radiotherapy, radiation is entirely or partially shielded by using a radiation collimator to obtain desired intensity modulated radiation or a modulator made by cutting using milling may be used.

The former has a possibility of generating an error due to malfunction of the collimator, it is difficult to calculate a scattered dose occurring in collimator gaps or leaves, and may increase a duration of treatment and uncertainty during the radiotherapy of moving organs.

Although the latter is free from the above disadvantages, it is difficult to be used in medical facilities due to severe noise from cutting process, generation of contaminated coolant water, need for a wide space to accommodate cutting facilities, and the difficulty of high-precision processing.

DETAILED DESCRIPTION OF THE INVENTIVE CONCEPT

Technical Problem

One or more embodiments of the present invention relate to a method and apparatus for manufacturing a radiation beam intensity modulator, capable of manufacturing a radiation beam intensity modulator rapidly and precisely by using a three-dimensional (3D) printer. One or more embodiments of the present invention relate to a method and apparatus for manufacturing a radiation beam intensity modulator, capable of reducing an error between a designed structure and an actually manufactured modulator by using a 3D printer and being free from problems such as contamination or occupying of a large space during manufacturing processes.

Technical Solution

According to an embodiment of the present invention, there is provided a method of manufacturing a radiation beam intensity modulator, the method including: obtaining dose modulation information expressed as a density matrix or three-dimensional (3D) structure information provided from a radiotherapy treatment planning system; obtaining design condition information of a radiation beam intensity modulator provided from the radiotherapy treatment planning system; generating a radiation beam intensity modulator structure based on the design condition information of the radiation beam intensity modulator and the dose modulation information expressed as the density matrix or the 3D structure information; adjusting the radiation beam intensity modulator structure by comparing at least one of an actual manufacturing condition and a treatment condition with the design condition information of the radiation beam intensity modulator; and manufacturing the radiation beam intensity modulator based on the radiation beam intensity modulator structure that is adjusted.

The design condition information of the radiation beam intensity modulator may include at least one of a distance between a source and the radiation beam intensity modulator, a location of a beam center axis, a location where the radiation beam intensity modulator is actually placed, and physical information of the radiation beam intensity modulator.

The adjusting of the radiation beam intensity modulator structure may include: comparing design material information obtained from the design condition information with manufacturing material information obtained from actual manufacturing condition; when degrees of radiation attenuation of the design material and the manufacturing material are equal to each other, maintaining a thickness of the radiation beam intensity modulator; and when degrees of radiation attenuation of the design material and the manufacturing material are different from each other, adjusting a thickness of the radiation beam intensity modulator according to a difference between the degrees of radiation attenuation.

The adjusting of the radiation beam intensity modulator structure may include: comparing distance information between a source and the radiation beam intensity modulator in design obtained from the design condition information with distance information between a source and the radiation beam intensity modulator during treatment obtained from the actual treatment condition; when the distance information between the source and the radiation beam intensity modulator in the design and during the treatment is constant, maintaining a size of the radiation beam intensity modulator; and when the distance information between the source and the radiation beam intensity modulator in the design and during the treatment is different, adjusting the size of the radiation beam intensity modulator according to a difference between the distance information.

The manufacturing of the radiation beam intensity modulator may be performed by using a 3D printer.

The manufacturing of the radiation beam intensity modulator may include: converting information of the adjusted radiation beam intensity modulator structure into information from which the 3D printer is capable of manufacturing the radiation beam intensity modulator; and when the information of the radiation beam intensity modulator structure is partially lost during the conversion, correcting a lost part.

According to an embodiment of the present invention, there is provided an apparatus for manufacturing a radiation beam intensity modulator, the apparatus including: a radiotherapy treatment planning system configured to design a radiation beam intensity modulator according to a radiotherapy treatment plan; a radiation beam intensity modulator modelling system configured to model the radiation beam intensity modulator based on information about the radiation beam intensity modulator designed by the radiotherapy treatment planning system; and a three-dimensional (3D) printer configured to manufacture the radiation beam intensity modulator based on the radiation beam intensity modulator modeled by the radiation beam intensity modulator modeling system, wherein the radiation beam intensity modulator modeling system includes: an input interface configured to obtain dose modulation information expressed as a density matrix or 3D structure information provided from the radiotherapy treatment planning system and to obtain design condition information of the radiation beam intensity modulator; a modulator structure generator configured to generate a radiation beam intensity modulator structure based on the design condition information of the radiation beam intensity modulator and the dose modulation information expressed as the density matrix or the 3D structure information; and a modulator structure adjustor configured to adjust the radiation beam intensity modulator structure by comparing at least one of an actual manufacturing condition and a treatment condition with the design condition information of the radiation beam intensity modulator.

Advantageous Effects

As described above, according to a method and apparatus for manufacturing a radiation beam intensity modulator of the present invention, a radiation beam intensity modulator may be rapidly and precisely manufactured by using a three-dimensional (3D) printer, and problems such as contamination or occupying of a large space during manufacturing processes may be prevented.

According to the radiation beam intensity modulator manufactured by the method and apparatus for manufacturing the radiation beam intensity modulator, there is no possibility of generating an error due to malfunction of a radiation collimator, and an error due to a scattered dose generating from the radiation collimator gaps or leaves, etc. Therefore, if the radiotherapy is performed by using the radiation beam intensity modulator manufactured according to the present invention, a duration of treatment may be greatly reduced as compared with the conventional therapy using the collimator, and the intensity modulated beam may be precisely irradiated with respect to moving organs.

Also, the method and apparatus for manufacturing the radiation beam intensity modulator according to the present invention do not generate environmental degradation elements such as noise and contaminated coolant water when compared with the conventional method of manufacturing the modulator through cutting, the modulator may be manufactured within a narrow space, and precision processing is available which prevents micromachining errors due to the cutting tool.

Also, according to the method and apparatus for manufacturing the radiation beam intensity modulator, the radiation beam intensity modulator may be manufactured by using metal that is effective in radiation shielding, as well as tissue-equivalent materials.

DESCRIPTION OF THE DRAWINGS

FIG. 17 is a flowchart illustrating a method of verifying a radiation beam intensity modulator according to an embodiment of the present invention.

BEST MODE

Hereinafter, embodiments of a method and apparatus for manufacturing and a radiation beam intensity modulator according to the present invention will be described in detail with reference to the accompanying drawings.

Figure 1:
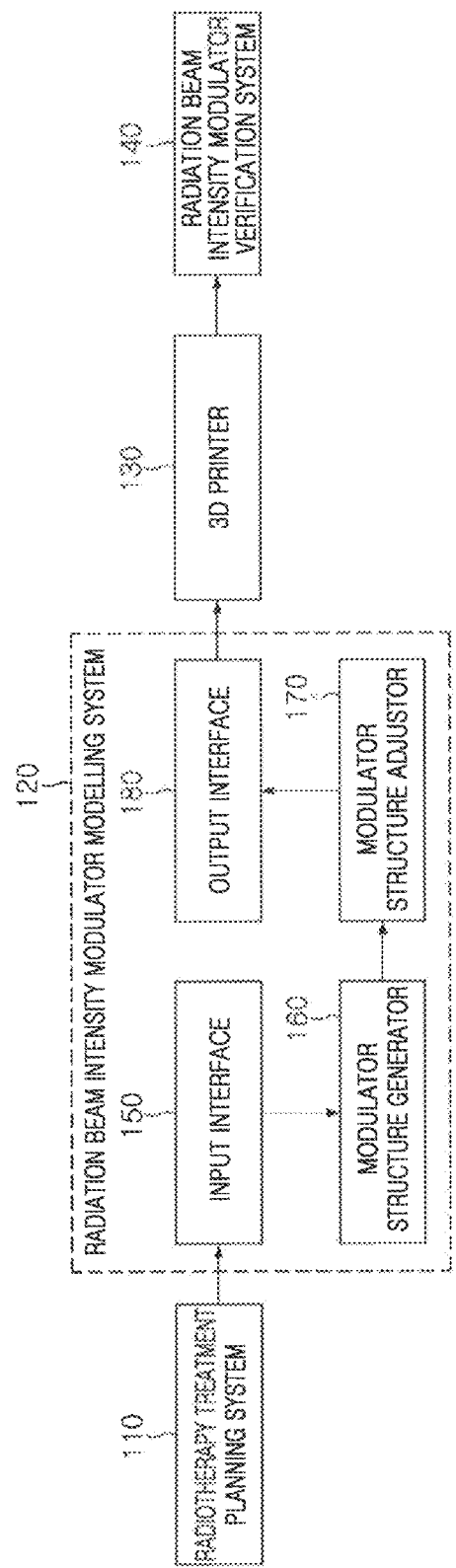
FIG. 1 is a block diagram of a system for manufacturing a radiation beam intensity modulator and a verification system according to an embodiment of the present invention.

FIG. 1 is a block diagram of a system for manufacturing a radiation beam intensity modulator and a verification system according to an embodiment of the present invention.

Referring to FIG. 1, a system for manufacturing and verifying a radiation beam intensity modulator includes a radiotherapy treatment planning system 110, a radiation beam intensity modulator modeling system 120, a three-dimensional (3D) printer 130, and a radiation beam intensity modulator verification system 140. The radiation beam intensity modulator modeling system 120 includes an input interface 150, a modulator structure generator 160, a modulator structure adjusting unit 170, and an output interface 180.

A medical team may establish a radiotherapy treatment plan on a patient based on medical images (CT, MRI images, etc.) and diagnosis information of the patient to be treated. The radiotherapy treatment planning system 110 may design a radiation beam intensity modulator according to the medical images of the patient and the established treatment plan.

The radiation beam intensity modulator modeling system 120 may model the radiation beam intensity modulator based on information about the radiation beam intensity modulator designed by the radiotherapy treatment planning system 110. The radiation beam intensity modulator modeling system 120 may model a radiation beam intensity modulator to be actually manufactured based on at least one of actual manufacturing conditions and treatment conditions. The input interface 150 obtains dose modulation information or 3D structure information expressed as a density matrix from radiation beam intensity modulator design information in the radiotherapy treatment planning system 110, and obtains design condition information of the radiation beam intensity modulator.

The modulator structure generator 160 generates a structure of the radiation beam intensity modulator based on the design condition information of the radiation beam intensity modulator and the dose modulation information or 3D structure information expressed as the density matrix, and the modulator structure adjusting unit 170 adjusts the generated structure of the radiation beam intensity modulator by comparing at least one of actual manufacturing condition or treatment condition with the design condition information of the radiation beam intensity modulator. The output interface 180 converts the information of the radiation beam intensity modulator structure adjusted by the modulator structure adjusting unit 170 into information allowing manufacturing of the 3D printer 130.

The 3D printer 130 prints and manufactures the radiation beam intensity modulator based on the radiation beam intensity modulator modeled by the radiation beam intensity modulator modeling system 120, and the radiation beam intensity modulator verification system 140 verifies accuracy of the radiation beam intensity modulator manufactured by the 3D printer 130 by comparing the radiation beam intensity modulator (that is, the radiation beam intensity modulator to be verified) manufactured by the 3D printer 130 and design information of the radiation beam intensity modulator (that is, original radiation beam intensity modulator) transmitted from the radiotherapy treatment planning system 110.

Hereinafter, processes of manufacturing the radiation beam intensity modulator by using the radiation beam intensity modulator manufacturing system of FIG. 1 will be described in detail below.

The radiotherapy treatment planning system 110 sets a region where the radiotherapy is to be performed and radiation beam intensity to be irradiated on the corresponding region according to medical images of a patient and established treatment plans, and designs the radiation beam intensity modulator based on the settings.

Figure 2A:
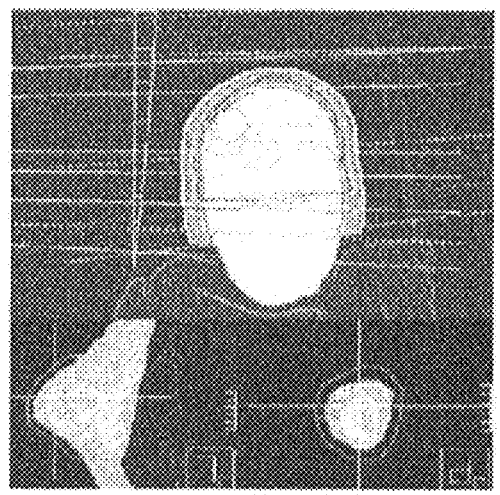
FIGS. 2A and 2B are diagrams showing kinds of a radiation beam intensity modulator.
Figure 2B:
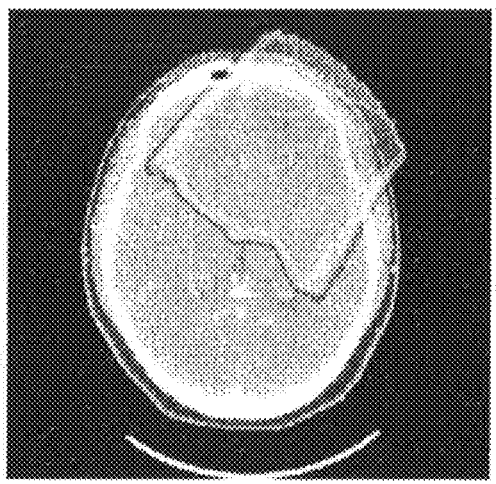

FIGS. 2A and 2B are diagrams exemplarily showing kinds of the of radiation beam intensity modulator, that is, FIG. 2A denotes the radiation beam intensity modulator designed for radiotherapy using X-ray as a source, and FIG. 2B shows a radiation beam intensity modulator designed for radiotherapy using proton as a source.

The radiotherapy treatment planning system 110 may design the radiation beam intensity modulator by using some of information obtained from the established treatment plan as the design conditions. For example, the design condition obtained from the treatment plan may include at least one of a distance between a source and the modulator, a location of a beam center axis, a location where the modulator is placed based on the location of the beam center axis, and a material forming the modulator.

According to an embodiment, the radiotherapy treatment planning system 110 may design the radiation beam intensity modulator as a 3D structure. Otherwise, the radiotherapy treatment planning system 110 may design the radiation beam intensity modulator as a shape of the density matrix representing the dose modulation information. For example, the radiotherapy treatment planning system 110 may express the radiation beam intensity modulator that is to be used in treating patients by generating a matrix including density values of dose modulation degree at each point.

Figure 3A:
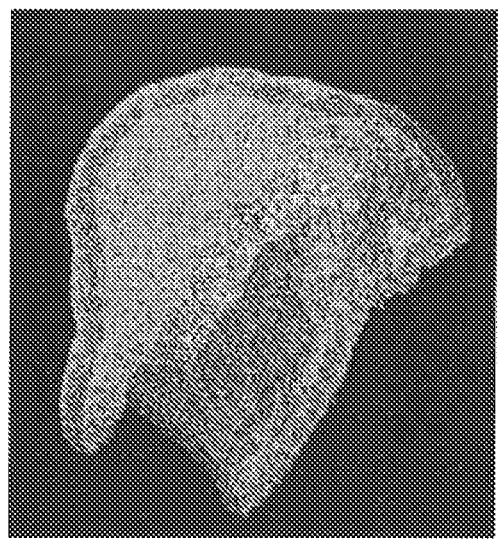
FIGS. 3A and 3B are diagrams showing dose modulation information expressed as a density matrix and three-dimensional (3D) structure information.
Figure 3B:
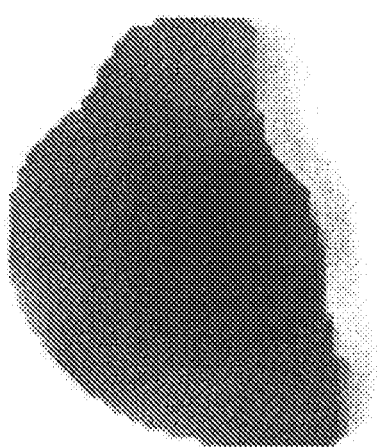

FIGS. 3A and 3B are diagrams showing dose modulation information and 3D structure information expressed as a density matrix, that is, FIG. 3A shows the radiation beam intensity modulator designed as a 3D structure, and FIG. 3B shows the radiation beam intensity modulator designed as a density matrix representing the dose modulation information.

When the design of the radiation beam intensity modulator is finished, the radiotherapy treatment planning system 110 transfers the information about the designed radiation beam intensity modulator to the radiation beam intensity modulator modeling system 120. For example, the radiotherapy treatment planning system 110 encodes the dose modulation information expressed as the density matrix or the 3D structure information together with the design condition information according to Digital Imaging and Communication in Medicine for Radiation Therapy (DICOM-RT) standard format, and then, may transfer the encoded information to the radiation beam intensity modulator modeling system 120.

When a file encoded according to the DICOM-RT standard format is received, the input interface 150 of the radiation beam intensity modulator modeling system 120 may obtain the dose modulation information expressed as the density matrix or the 3D structure information from the file. Also, the input interface 150 obtains the design condition information of the radiation beam intensity modulator, wherein the design condition information is stored in a header of the file.

The modulator structure generator 160 generates the radiation beam intensity modulator structure based on the design condition information of the radiation beam intensity modulator and the dose modulation information expressed as the density matrix or the 3D structure information.

Figure 4:
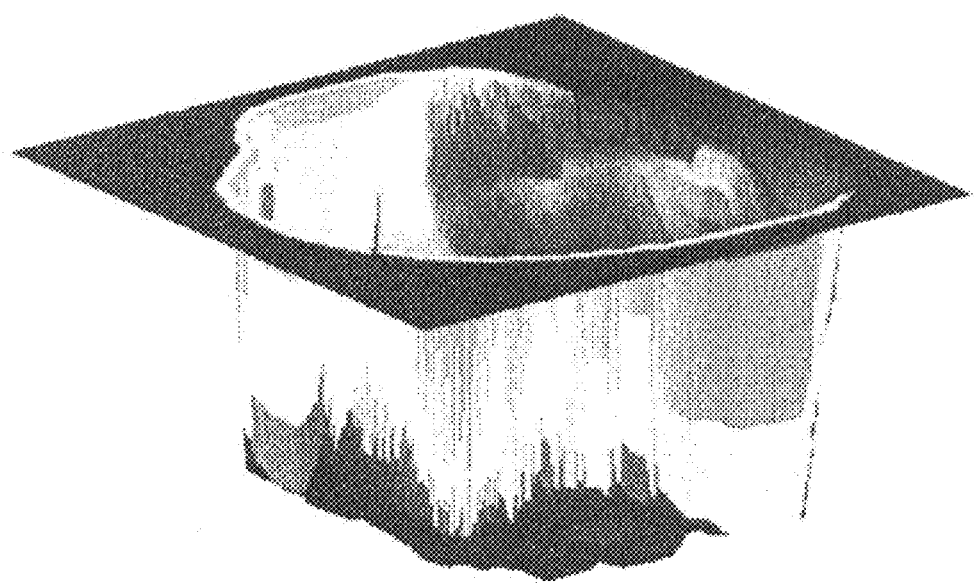
FIG. 4 is a diagram of a radiation beam intensity modulator structure generated based on dose modulation information.

FIG. 4 is a diagram of a radiation beam intensity modulator structure generated based on dose modulation information.

For example, when the dose modulation information expressed as the density matrix is transmitted, the modulator structure generator 160 may generate a radiation beam intensity modulator structure having a depth corresponding to the dose modulation value based on the dose modulation value at each point in the matrix.

When the radiation beam intensity modulator structure is generated, the modulator structure adjusting unit 170 adjusts the radiation beam intensity modulator structure generated by the modulator structure generator 160 by comparing at least one of the actual manufacturing condition and the treatment condition with the design condition information. The actual manufacturing condition and the treatment condition may be input by a user taking into account manufacturing status and treatment status.

MODE OF THE INVENTION

Figure 5:
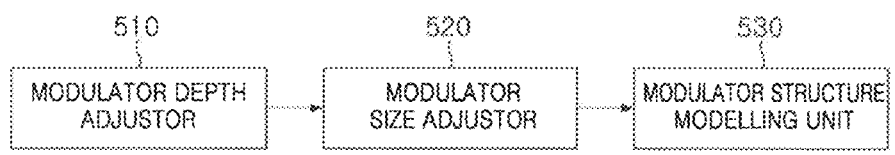
FIG. 5 is a block diagram of a modulator structure adjusting unit according to an embodiment of the present invention.

FIG. 5 is a block diagram of a modulator structure adjusting unit according to an embodiment of the present invention.

Referring to FIG. 5, the modulator structure adjusting unit 170 includes a modulator thickness adjuster 510, a modulator size adjuster 520, and a modulator structure modeling unit 530.

The modulator thickness adjuster 510 adjusts a thickness of the radiation beam intensity modulator by comparing designed material information obtained from the design condition information with manufacturing material information obtained from the actual manufacturing condition. As a result of comparison, degrees of radiation attenuation of the designed material and the manufacturing material are equal to each other, the modulator thickness adjuster 510 maintains the depth of the radiation beam intensity modulator generated by the modulator structure generator 160. For example, in a case where the degrees of radiation attenuation of both materials are equal to each other based on physical information (density, electron density, stopping power, etc.) of the designed material and the manufacturing material, the thickness of the radiation beam intensity modulator may be maintained.

As a result of comparison, when the degrees of radiation attenuation of the designed material and the manufacturing material are different from each other, the modulator thickness adjuster 510 adjusts the thickness of the radiation beam intensity modulator generated by the modulator structure generator 160 according to a difference between the degrees of radiation attenuation of the materials. For example, in a case where a degree of radiation attenuation of the actual manufacturing material per thickness is 5% (that is, 5%/cm) whereas a degree of radiation attenuation of the designed material per thickness is 10% (that is, 10%/cm (thickness)), the modulator thickness adjuster 510 may adjust the thickness of the radiation beam intensity modulator generated by the modulator structure generator 160 to be doubled.

The modulator size adjuster 520 adjusts the size of the radiation beam intensity modulator by comparing information about a distance between a source and the modulator obtained from the design condition information with information about a distance between a source and the modulator during treatment obtained from the actual manufacturing condition.

Figure 6:
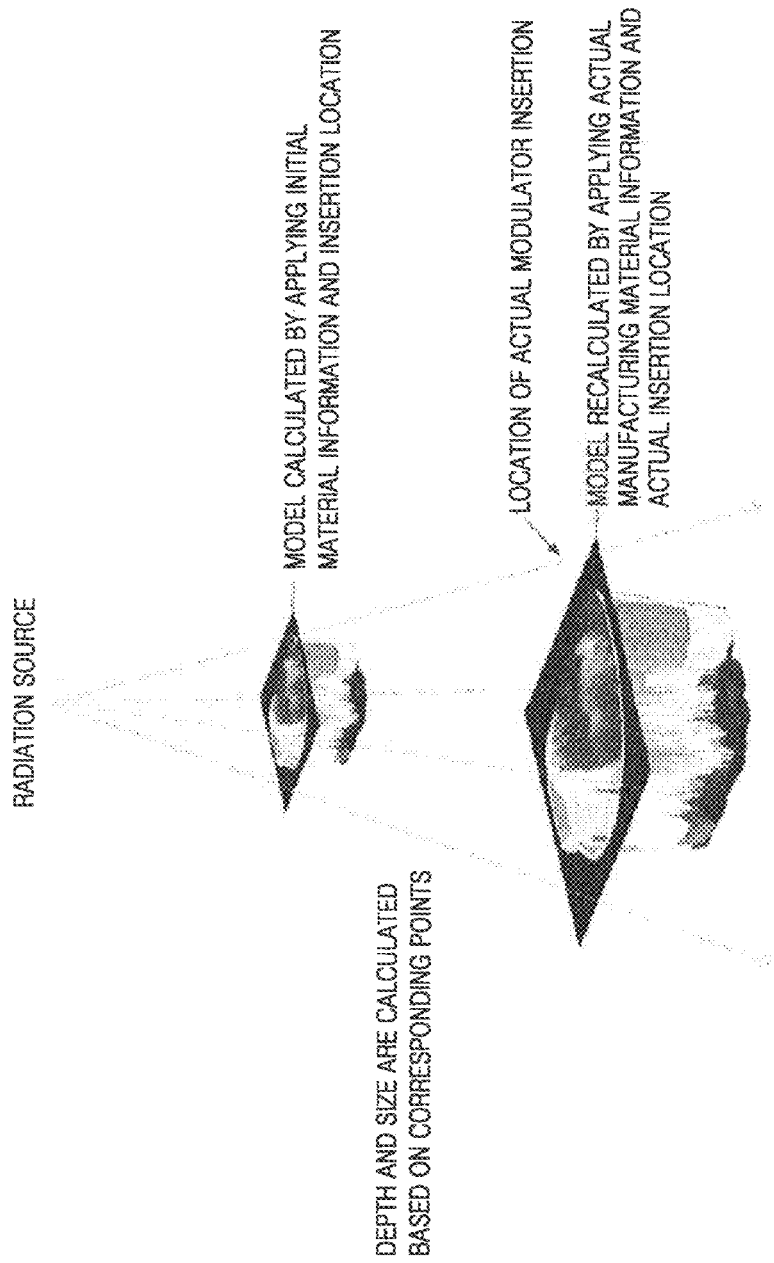
FIG. 6 is a diagram exemplarily illustrating a method of adjusting a size of a modulator.

FIG. 6 is a diagram exemplarily illustrating a method of adjusting the size of the modulator in the modulator size adjuster.

As a result of comparing the distance information, when the distance between the source and the modulator in the design and the distance between the source and the modulator during the treatment are equal to each other, the modulator size adjuster 520 maintains the size of the radiation beam intensity modulator. As a result of comparing the distance information, when the distance between the source and the modulator in the design and the distance between the source and the modulator during the treatment are different from each other, the modulator size adjuster 520 adjusts the size of the radiation beam intensity modulator according to a difference between the distances. For example, if the distance between the source and the modulator based on an actual insertion location of the modulator is twice or more as large as the distance between the source and the modulator in the design, the modulator size adjuster 520 may double the size of the radiation beam intensity modulator.

Figure 7:
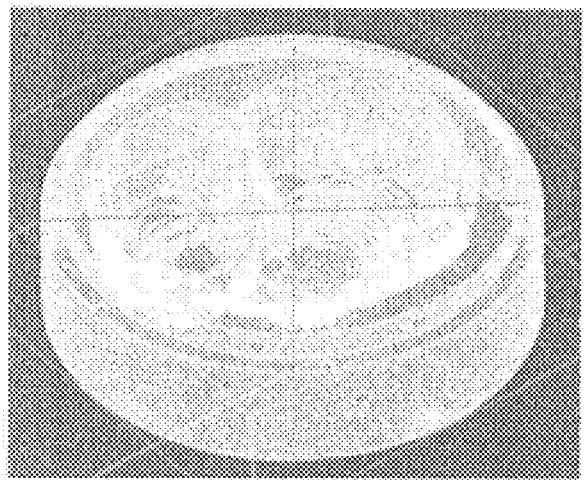
FIG. 7 is a diagram of a radiation beam intensity modulator modeled to be used in actual therapy.

The modulator structure modeling unit 530 may model the radiation beam intensity modulator so that the radiation beam intensity modulator, the thickness and the size of which are adjusted by the modulator size adjuster 520, may be used in actual treatment. FIG. 7 is a diagram of a radiation beam intensity modulator modeled to be used in actual treatment.

In one embodiment, the modulator structure modeling unit 530 may perform modeling by adding a support wall (side wall) to the radiation beam intensity modulator so that the 3D printer 130 may print the modulator. For example, the modulator structure modeling unit 530 may perform modeling of the radiation beam intensity modulator by adding a support wall to the radiation beam intensity modulator along with an outermost surface of the radiation beam intensity modulator.

Also, the modulator structure modeling unit 530 may perform modeling by adding a mounting portion that allows the radiation beam intensity modulator to be mounted in a radiotherapy machine (not shown). For example, in a case where a radiotherapy machine to be used in actual treatment is defined, the modulator structure modeling unit 530 may perform modeling of the radiation beam intensity modulator by adding a mounting portion of a predetermined shape according to a kind of the radiotherapy machine.

In another embodiment, in a case of a radiation beam intensity modulator of an attached type to skin of a patient, the radiation beam intensity modulator that is manufactured may be cut to be attached to the skin of the patient. In this case, the modulator structure modeling unit 530 may perform modeling of the radiation beam intensity modulator by adding a cutting surface so that the radiation beam intensity modulator may be easily cut.

In one embodiment, the modulator structure modeling unit 530 may perform modeling of the radiation beam intensity modulator by adding patient identification information to the radiation beam intensity modulator. For example, the modulator structure modeling unit 530 may perform modeling of the radiation beam intensity modulator so that patient identification information (e.g., at least one of patient ID, ID number, and name) may be printed on a side surface or an attaching portion of the radiation beam intensity modulator. A medical team may identify a patient on which the corresponding radiation beam intensity modulator is to be used, by using the patient identification information printed on the radiation beam intensity modulator during actual treatment.

In one embodiment, the modulator structure modeling unit 530 may perform modeling of the radiation beam intensity modulator by adding a mounting location line based on a beam center point. When the manufactured radiation beam intensity modulator is mounted in the therapy machine or body of the patient, the medical team may attach the modulator at a precise location based on the mounting location line printed on the modulator.

Figure 8:
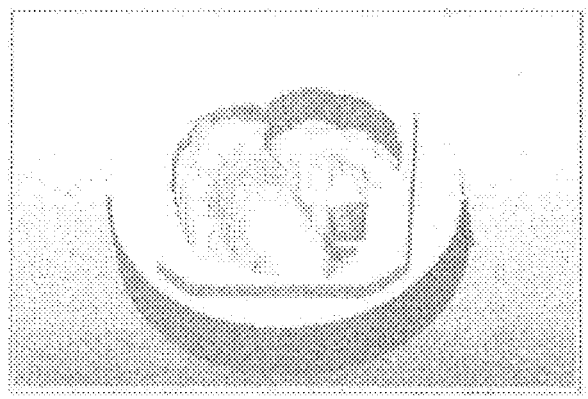
FIG. 8 is a diagram showing a radiation beam intensity modulator structure of a file converted to be recognized by a three-dimensional (3D) printer.

The output interface 180 converts the information of the radiation beam intensity modulator structure adjusted by the modulator structure adjusting unit 170 into information allowing manufacturing of the 3D printer 130. FIG. 8 is a diagram showing a radiation beam intensity modulator structure of a file converted to be recognized by a three-dimensional (3D) printer.

For example, the output interface 180 may convert information about the radiation beam intensity modulator structure into a file recognizable by the 3D printer 130 such as an STL file, a CAD file, etc.

In one embodiment, during the process of converting the information to the file recognizable by the 3D printer 130, some of the information about the radiation beam intensity modulator may be loss. In this case, the output interface 180 may correct lost information in the radiation beam intensity modulator structure. For example, the output interface 180 may correct the lost part through interpolation. That is, the output interface 180 may estimate a value at a point where the information is lost by interpolating values at the other points where the information is not lost.

In one embodiment, the output interface 180 may designate an order of manufacturing the radiation beam intensity modulator taking into account complexity of the radiation beam intensity modulator structure or a total manufacturing time duration, and may include the order in the file. For example, the output interface 180 may set the radiation beam intensity modulator may be printed from a left side towards a right side, or from an upper side towards a lower side. Otherwise, the output interface 180 may set a printing order from a certain part to a final part, or may set the printing order so that the radiation beam intensity modulator may be manufactured in a stood type.

In one embodiment, the output interface 180 may allow information about the radiation beam intensity modulator, a patient, or a therapy machine such as 3D structure information, a location coordinate, physical information of the radiation beam intensity modulator, patient identification information, therapy machine information, or examination port, to be included in the file in order to prevent an error from generating during the manufacturing process.

The 3D printer 130 may print and manufacture the radiation beam intensity modulator based on the file provided by the output interface 180 of the radiation beam intensity modulator modeling system 120.

Figure 9A:
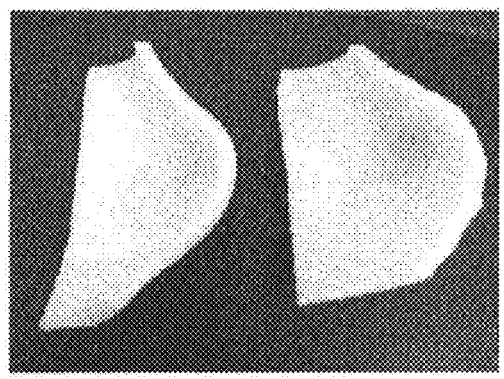
FIGS. 9A and 9B are diagrams of a radiation beam intensity modulator that is manufactured.
Figure 9B:
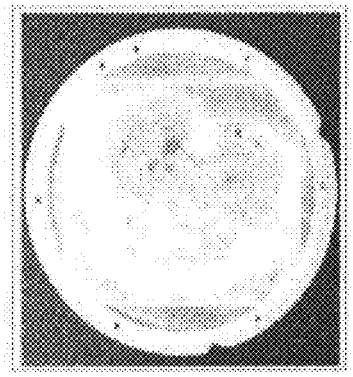

FIGS. 9A and 9B are diagrams of a radiation beam intensity modulator that is manufactured. FIG. 9A shows a radiation beam intensity modulator manufactured from the 3D structure format, and FIG. 9B shows a radiation beam intensity modulator manufactured from the density matrix format representing the dose modulation information.

Figure 10:
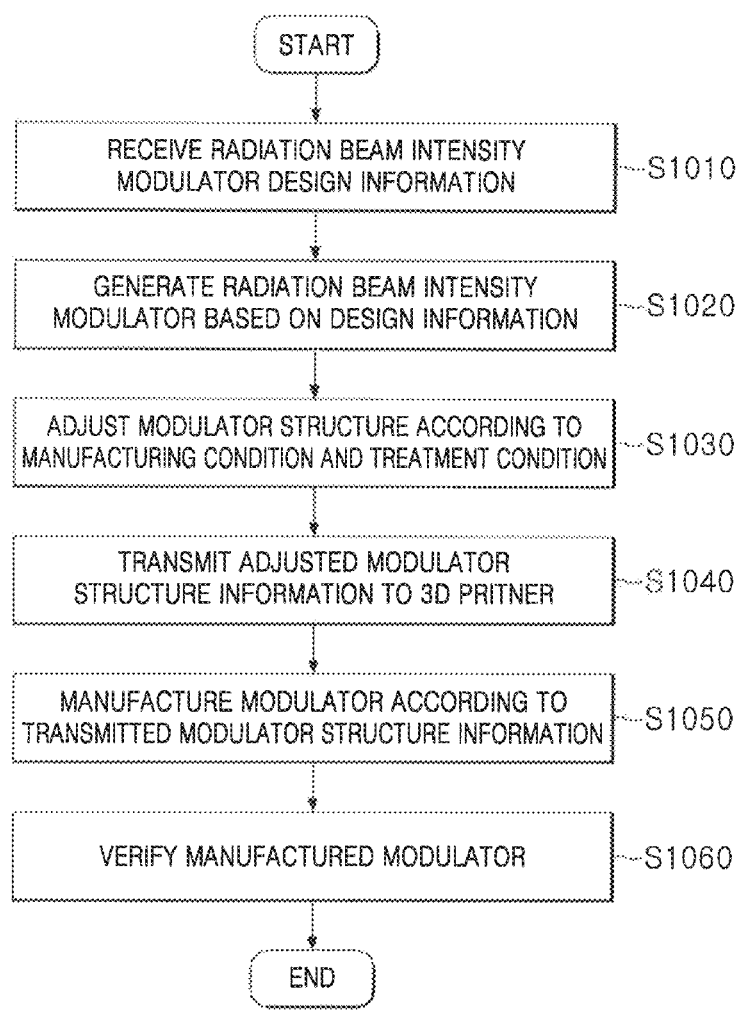
FIG. 10 is a flowchart illustrating a method of manufacturing and verifying a radiation beam intensity modulator according to an embodiment of the present invention.

FIG. 10 is a flowchart illustrating a method of manufacturing and verifying a radiation beam intensity modulator according to an embodiment of the present invention.

Referring to FIG. 10, according to the method of manufacturing the radiation beam intensity modulator according to an embodiment, the treatment planning system 110 designs the radiation beam intensity modulator. In one embodiment, the treatment planning system may design the radiation beam intensity modulator as a density matrix representing a dose modulation information or a 3D structure form. The input interface 150 of the radiation beam intensity modulator modeling system 120 receives radiation beam intensity modulator design information from the treatment planning system 110 (S1010). In one embodiment, the treatment planning system 110 may encode the radiation beam intensity modulator design information according to the DICOM-RT standard format and transfer the encoded information to the input interface.

The input interface 150 obtains the design condition information and the dose modulation information expressed as the density matrix, or 3D structure information from the radiation beam intensity modulator design information provided from the treatment planning system 110, and the modulator structure generator 160 generates the radiation beam intensity modulator based on the obtained information (S1020).

When the radiation beam intensity modulator structure is generated, the modulator structure adjusting unit 170 adjusts the radiation beam intensity modulator structure by comparing at least one of the actual manufacturing condition and the treatment condition with the design condition information (S1030).

Figure 11:
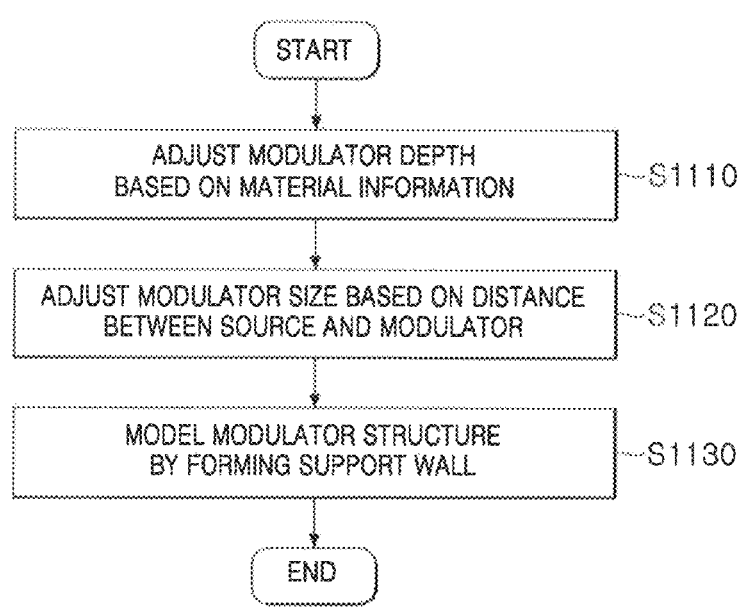
FIG. 11 is a flowchart illustrating a method of adjusting a structure of the modulator according to an embodiment of the present invention.

FIG. 11 is a flowchart illustrating a method of adjusting a modulator structure according to an embodiment of the present invention.

Referring to FIG. 11, the modulator structure adjusting unit 170 adjusts a thickness of the radiation beam intensity modulator based on material information (S1110). For example, the modulator structure adjusting unit 170 compares the designed material information obtained from the design condition information with the manufacturing material information obtained from the actual manufacturing condition. Then, when degrees of radiation attenuation of the designed material and the manufacturing material are equal to each other, the thickness of the generated radiation beam intensity modulator is maintained, and when the degrees of radiation attenuation of the designed material and the manufacturing material are different from each other, the thickness of the generated radiation beam intensity modulator is adjusted according to a difference between the degrees of radiation attenuation.

The modulator structure adjusting unit 170 adjusts the size of the radiation beam intensity modulator based on information about a distance between a source and the modulator (S1120). For example, the modulator structure adjusting unit 170 compares the designed distance information between the source and the modulator obtained from the design condition information with the actual distance information between the source and the modulator obtained from the actual treatment condition, and when they are equal to each other, the modulator structure adjusting unit 170 maintains the size of the generated radiation beam intensity modulator, and when they are different from each other, the modulator structure adjusting unit 170 adjusts the size of the radiation beam intensity modulator according to the difference between the distances.

The modulator structure adjusting unit 170 performs modeling of the radiation beam intensity modulator by adding a support wall (side wall) to the radiation beam intensity modulator so that the 3D printer 130 may print the radiation beam intensity modulator (S1130).

Referring back to FIG. 10, when the radiation beam intensity modulator structure is adjusted, the output interface 180 of the radiation beam intensity modulator modeling system 120 transmits information about the adjusted radiation beam intensity modulator structure to the 3D printer 130 (S1040). In one embodiment, the output interface 180 transmits the information about the adjusted radiation beam intensity modulator structure after converting the information into information that the 3D printer 130 may manufacture.

The 3D printer 130 manufactures the radiation beam intensity modulator based on the information about the radiation beam intensity modulator structure (S1050). When the radiation beam intensity modulator is manufactured, the manufactured radiation beam intensity modulator is verified by the radiation beam intensity modulator verification system 140 before actually being used in treatment (S1060).

Figure 12:
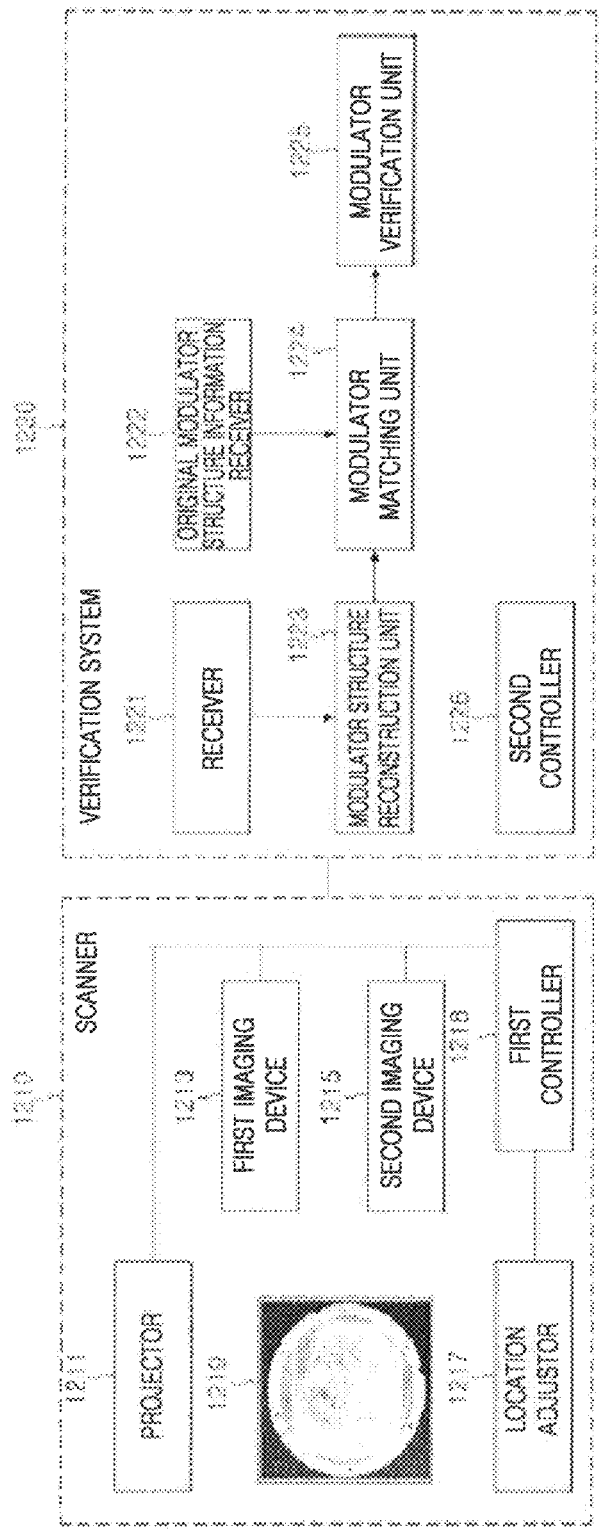
FIG. 12 is a block diagram of a system for verifying a radiation beam intensity modulator according to an embodiment of the present invention.

FIG. 12 is a block diagram of a system for verifying a radiation beam intensity modulator according to an embodiment of the present invention.

Referring to FIG. 12, the radiation beam intensity modulator verification system 140 may include a scanner 1210 and a verification system 1220. The scanner 1210 includes a projector 1211, a first imaging device 1213, a second imaging device 1215, a location adjustor 1217, and a first controller 1218, and the verification system 1220 includes a data receiver 1221, an original modulator structure information receiver 1222, a modulator structure reconstruction unit 1223, a modulator matching unit 1224, a modulator verification unit 1225, and a second controller 1226.

The scanner 1210 scans a radiation beam intensity modulator 1219 (hereinafter, verification target radiation beam intensity modulator) manufactured by the radiation beam intensity modulator manufacturing system to obtain an image of the radiation beam intensity modulator 1219, and generates 3D structure information of the radiation beam intensity modulator 1219 based on the image. The verification system 1220 verifies the verification target radiation beam intensity modulator based on the 3D structure information of the verification target radiation beam intensity modulator transmitted from the scanner 1210 and the original radiation beam intensity modulator information.

Figure 13:
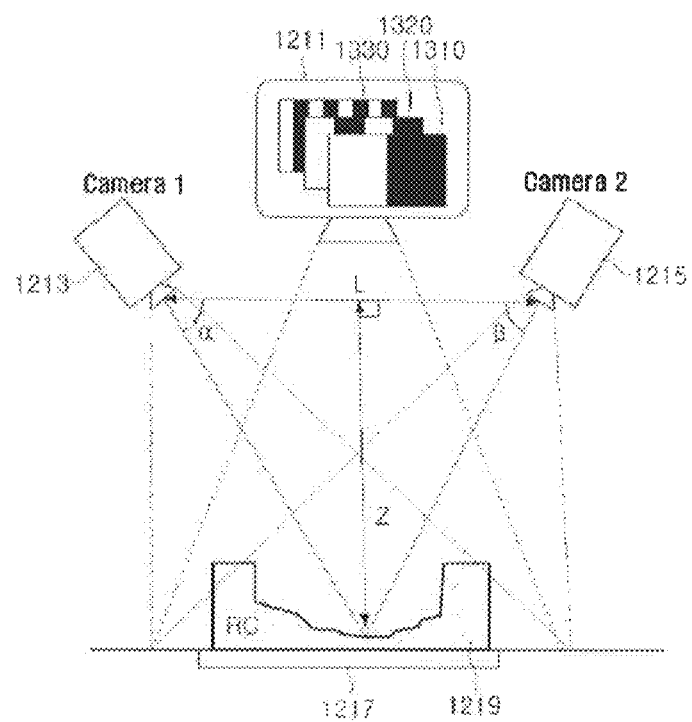
FIG. 13 is a block diagram of a scanner according to an embodiment of the present invention.
Figure 14:
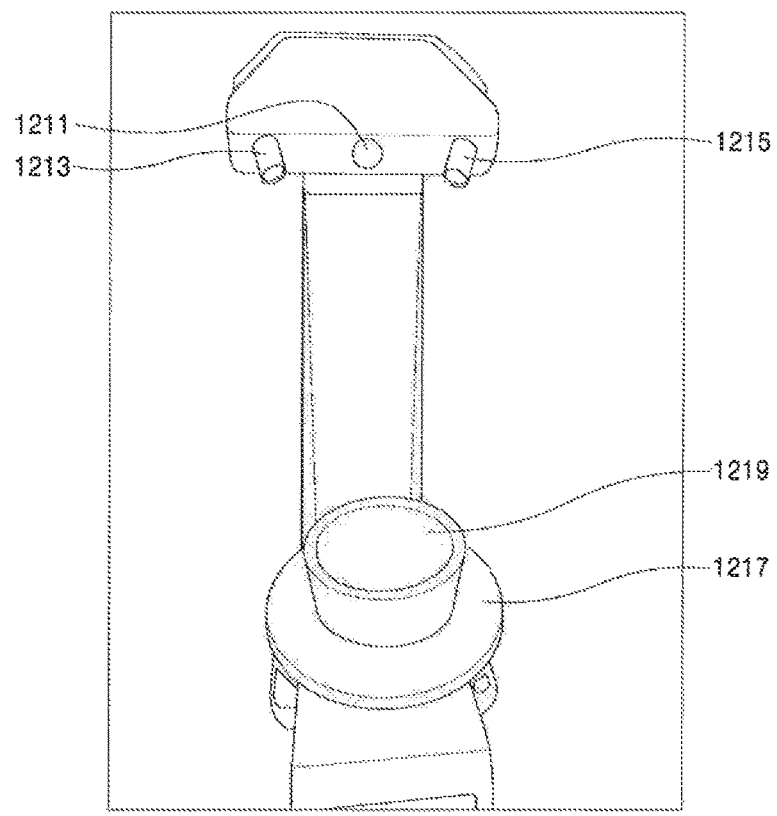
FIG. 14 is a diagram of a scanner manufactured according to an embodiment of the present invention.

FIG. 13 is a block diagram of a scanner according to an embodiment of the present invention, and FIG. 14 is a diagram of a scanner manufactured according to an embodiment of the present invention.

Hereinafter, operations of the scanner will be described in detail with reference to FIGS. 12 to 14.

The projector 1211 projects at least one pattern image to the verification target radiation beam intensity modulator. According to an embodiment, the projector 1211 sequentially projects one or more pattern images having different gaps among patterns, so that every part of the verification target radiation beam intensity modulator may be photographed. For example, the projector 1211 sequentially projects a first pattern image 1310, a second pattern image 1320, and a third pattern image 1330 having different gaps among patterns from one another, so that a part that has not been photographed when a certain pattern image is projected may be photographed when another pattern image is projected. By sequentially projecting one or more pattern images having different gaps among the patterns, the scanner may scan a region having a high depth-gradient in the radiation beam intensity modulator. In one embodiment, the projector 1211 may project the pattern images by using blue light-emitting diode (LED) as a light source.

The first imaging device 1213 and the second imaging device 1215 photograph the verification target radiation beam intensity modulator to which the pattern images are projected. For example, the first imaging device 1213 and the second imaging device 1215 may correspond to stereo cameras photographing an object on a same line. The first imaging device 1213 and the second imaging device 1215 transmit the captured images to the first controller 1218.

The location adjustor 1217 adjusts a photographing location of the verification target radiation beam intensity modulator 1219. In one embodiment, the location adjustor 1217 may include a location adjusting device of a turn-table type. For example, the location adjustor 1217 may adjust the photographing location of the verification target radiation beam intensity modulator 1219 located on a turn-table, by rotating, moving in back-and-forth and left-and-right directions, or tilting the turn-table. For example, the location adjustor 1217 may adjust the verification target radiation beam intensity modulator 1219 by rotating the turn-table by 360° (±180°) angle based on a vertical axis and tilting the turn-table by 90° (±45°) based on a horizontal axis.

In one embodiment, the location adjustor 1217 may adjust the photographing location of the verification target radiation beam intensity modulator 1219 according to a predetermined pattern, or in a case where there is a region that has not been reconstructed in the verification system 120, the location adjustor 1217 may automatically adjust the photographing location of the verification target radiation beam intensity modulator 1219 so that the corresponding region may be photographed. Otherwise, the location adjustor 1217 may manually adjust the photographing location by the user. For example, the location adjustor 1217 may adjust the photographing location by rotating, moving in the back-and-forth and left-and-right directions, or tilting the turn-table so as to photograph a certain region by a manual operation of the user.

The first controller 1218 calculates the 3D structure of the verification target radiation beam intensity modulator based on the images of the verification target radiation beam intensity modulator captured by the first and second imaging devices 1213 and 1215. For example, the first controller 1218 may calculate the 3D structure of the verification target radiation beam intensity modulator as a depth matrix form based on captured stereo images.

In one embodiment, the first controller 1218 may calculate a depth value at a certain point in the verification target radiation beam intensity modulator by using a phase-shifting optical triangulation method. The depth value may be calculated as follows.

Referring to FIG. 13, a distance L between the first imaging device 1213 and the second imaging device 1215 may be expressed by following equation 1.

$$L = \frac{Z}{\tan(\alpha)} + \frac{Z}{\tan(\beta)} \quad \text{[Equation 1]}$$

A vertical distance Z (that is, a depth of a certain point) from a horizontal fine between the first imaging device 1213 and the second imaging device 1215 to the certain point of the verification target radiation beam intensity modulator 1219 may be calculated by following equation 2.

$$Z = L \bigg/ \left(\frac{1}{\tan(\alpha)} + \frac{1}{\tan(\beta)}\right) = \frac{L\sin(\alpha)\sin(\beta)}{\sin(\alpha+\beta)} \quad \text{[Equation 2]}$$

α denotes an angle between the horizontal line between the first imaging device 1213 and the second imaging device 1215 and a connection line connecting the first imaging device 1213 to a certain point of the radiation beam intensity modulator 1219, and β denotes an angle between the horizontal line between the first imaging device 1213 and the second imaging device 1215 and a connection line connecting the second imaging device 1215 to a certain point of the radiation beam intensity modulator 1219.

Since the distance L between the first imaging device 1213 and the second imaging device 1215 is preset according to specification of the scanner, the first controller 1218 may calculate the depth value at the certain point of the verification target radiation beam intensity modulator by calculating values of α and β at the certain point.

The first controller 1218 calculates the depth value at every point in the verification target radiation beam intensity modulator by the above-described method, and generates a matrix by matching a coordinate (x, y) at a point to a depth value z in Cartesian coordinates. That is, the first controller 1218 may reconstruct the 3D structure of the verification target radiation beam intensity modulator as a depth matrix form on the Cartesian coordinates.

The first controller 1218 may convert the 3D structure information (or data) of the verification target radiation beam intensity modulator into a file, and transmit the file to the verification system 1220. For example, the first controller 1218 may convert the 3D structure information of the verification target radiation beam intensity modulator into a CAD file such as an STL file, and then, transmits the file. Kinds of the file are not limited thereto, provided that the file format is suitable for processing and analyzing images.

The embodiment, in which the first controller 1218 included in the scanner 1210 calculates the 3D structure of the verification target radiation beam intensity modulator based on the images of the verification target radiation beam intensity modulator, is described above, but according to another embodiment, the scanner 1210 may transmit the captured images of the verification target radiation beam intensity modulator to the verification system 1220, and then, the verification system 1220 may calculate the 3D structure of the verification target radiation beam intensity modulator and use the 3D structure in matching of the radiation beam intensity modulator.

The 3D structure of the verification target radiation beam intensity modulator is calculated based on the images of the verification target radiation beam intensity modulator captured by the first and second imaging devices 1213 and 1215.

Figure 15:
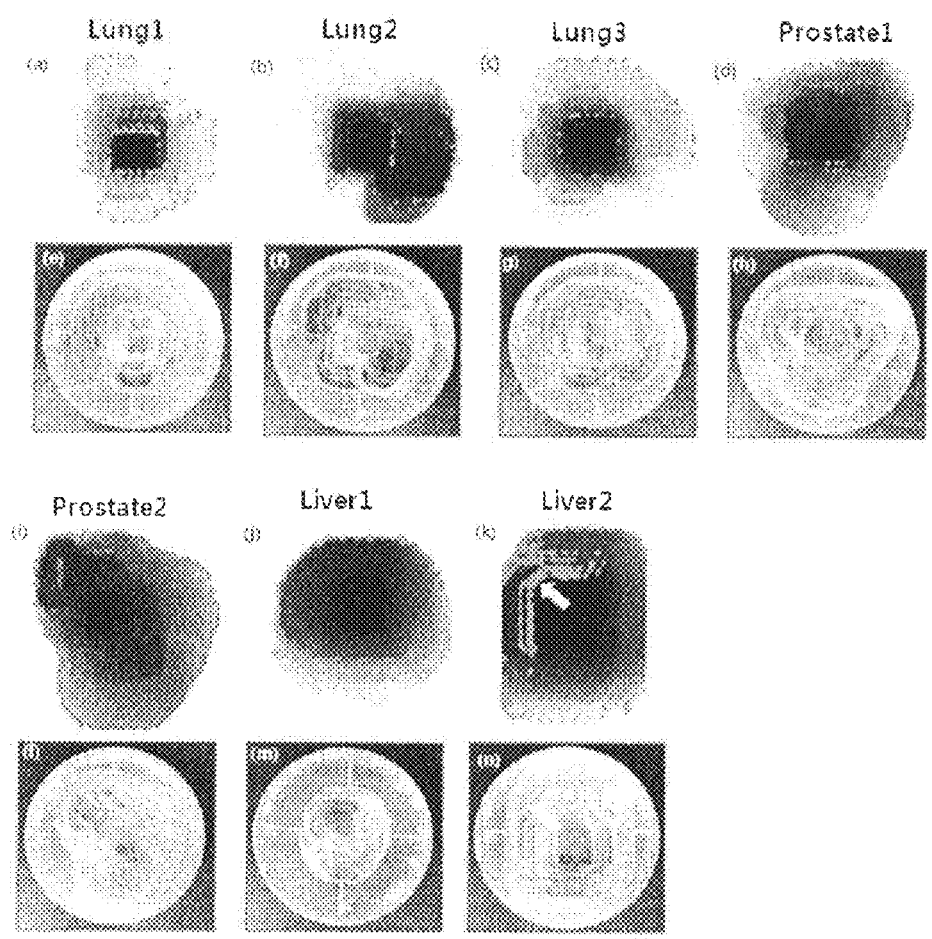
FIG. 15 is a diagram illustrating a method of matching a radiation beam intensity modulator to be verified with an original radiation beam intensity modulator and a method of verifying the radiation beam intensity modulator to be verified.

FIG. 15 is a diagram illustrating a method of matching a verification target radiation beam intensity modulator with an original radiation beam intensity modulator and a method of verifying the verification target radiation beam intensity modulator. Hereinafter, a method of verifying the verification target radiation beam intensity modulator in the verification system 1220 will be described in detail below with reference to FIGS. 12 and 15.

The verification system 1220 verifies the verification target radiation beam intensity modulator based on the 3D structure information of the verification target radiation beam intensity modulator transmitted from the scanner 1210 and the original radiation beam intensity modulator information.

The receiver 1221 may receive the 3D structure information of the verification target radiation beam intensity modulator from the scanner 1210. For example, the receiver 1221 may receive a file including the 3D structure information of the verification target radiation beam intensity modulator from the first controller 1218.

The modulator structure reconstruction unit 1223 analyzes the 3D structure information of the verification target radiation beam intensity modulator received by the receiver 1221 to reconstruct the radiation beam intensity modulator. For example, the modulator structure reconstruction unit 1223 may analyze the file received by the receiver 1221 to reconstruct the verification target radiation beam intensity modulator in a thickness matrix form ((e) of FIG. 15). In one embodiment, the thickness matrix of the verification target radiation beam intensity modulator may be calculated by using the depth matrix of the verification target radiation beam intensity modulator and a bottom depth value of the verification target radiation beam intensity modulator.

The original modulator structure information receiver 1222 receives structure information of the original radiation beam intensity modulator. For example, the original modulator structure information receiver 1222 may receive the structure information of the original radiation beam intensity modulator from the radiotherapy treatment planning system 110. Otherwise, the structure of the radiation beam intensity modulator may be adjusted by the radiation beam intensity modulator modeling system 120, and thus, the original modulator structure information receiver 1222 may receive the structure information of the original radiation beam intensity modulator from the radiation beam intensity modulator modeling system 120. In one embodiment, the radiotherapy treatment planning system 110 or the radiation beam intensity modulator modeling system 120 may transmit the structure information of the original radiation beam intensity modulator after encoding the structure information according to the DICOM-RT standard format.

In one embodiment, the original modulator structure information receiver 1222 may generate a thickness matrix of the original radiation beam intensity modulator from the original radiation beam intensity modulator structure information, ((c) of FIG. 15)

The modulator matching unit 1224 matches the verification target radiation beam intensity modulator that has been reconstructed by the modulator structure reconstruction unit 1223 with the original radiation beam intensity modulator transmitted from the original modulator structure information receiver 1222, based on thickness information.

In one embodiment, the modulator matching unit 1224 obtains the thickness matrix from the 3D structure information of the verification target radiation beam intensity modulator and the structure information of the original radiation beam intensity modulator, and matches the verification target radiation beam intensity modulator and the original radiation beam intensity modulator with each other while varying corresponding points (overlapping points) between the radiation beam intensity modulators based on one of center points of the radiation beam intensity modulators, the beam isocenter, and well-known certain reference point, so that a difference between the thickness matrix of the radiation beam intensity modulators is minimized. For example, the modulator matching unit 1224 sets a center of points recognized from the verification target radiation beam intensity modulator as a beam isocenter, and may use the beam isocenter as a matching reference with a beam isocenter of the original radiation beam intensity modulator. In one embodiment, the modulator matching unit 1224 may recognize a plurality of holes that are located on an edge of the radiation beam intensity modulator and used to attach a metal ring for being mounted on a gantry of a radiotherapy treatment machine, and may set a center of the plurality of holes as the beam isocenter.

Here, the modulator matching unit 1224 may match the radiation beam intensity modulators so that the difference between the thickness matrix of the two radiation beam intensity modulators is minimized, by using the thickness matrix extracted from the original radiation beam intensity modulator structure information and the thickness matrix of the verification target radiation beam intensity modulator that has been reconstructed by the modulator structure reconstruction unit 1223.

The modulator matching unit 1224 calculates a maximum correlation coefficient (CC) between the verification target radiation beam intensity modulator and the original radiation beam intensity modulator based on the thickness, and matches the two radiation beam intensity modulators so that the calculated maximum CC is close to 1. Thus, the difference between the thickness matrix of the two radiation beam intensity modulators may be minimized. The maximum CC may be calculated by following equation 3.

$$CC = \frac{\sum_m \sum_n (PRC_{mn} - \overline{PRC})(MCR_{mn} - \overline{MRC})}{\sqrt{\left(\sum_m \sum_n (PRC_{mn} - \overline{PRC})^2\right)\left(\sum_m \sum_n (MCR_{mn} - \overline{MRC})^2\right)}} \quad \text{[Equation 3]}$$

Here, PRC denotes a thickness value of the original radiation beam intensity modulator, MRC denotes a thickness value of the reconstructed radiation beam intensity modulator, and m and n are integers (row and column of the matrix). $\overline{PRC}$ denotes an average of the PRC values in the matrix, and $\overline{MRC}$ denotes an average of the MRC values in the matrix.

The modulator matching unit 1224 varies corresponding points (overlapping points) between the thickness matrixes of the verification target radiation beam intensity modulator and the original radiation beam intensity modulator by moving locations of the thickness matrixes based on a reference point (center point, the beam isocenter, or a well-known certain reference point), and calculates the maximum CC at each location. The modulator matching unit 1224 calculates and compares the maximum CCs at the locations with one another, and then, may match the two depth matrixes to a location where the calculated maximum CC value is closest to 1.

The modulator verification unit 1225 may verify the verification target radiation beam intensity modulator based on the difference between the thicknesses of the matched radiation beam intensity modulators. In one embodiment, the modulator verification unit 1225 verifies the verification target radiation beam intensity modulator by evaluating whether the difference between the thicknesses of the matched radiation beam intensity modulators passes the standard through a depth difference (DD) analysis or a composite analysis (CA). The analysis method may be set by the user.

In one embodiment, when the verification method is set as the DD analysis, the modulator verification unit 1225 verifies the verification target radiation beam intensity modulator by evaluating whether the difference in thicknesses of the matched radiation beam intensity modulators passes a predetermined standard at each point.

In another embodiment, when the verification method is set as the CA, the modulator verification unit 1225 performs the CA at each point whether each point passes the standard to verify the verification target radiation beam intensity modulator. The modulator verification unit 1225 may performs the CA at each point by using following equation 4.

$$CA = \left\{ \sqrt{\frac{\text{Difference}^2}{(DD_{Tolerance})^2} + \frac{\text{Distance}^2}{(DTA_{Tolerance})^2}} \leq \right. \quad \text{[Equation 4]}$$

1: Pass or > 1: Fail

Here, CA denotes an evaluation value. When the CA value is less than 1, it is evaluated that a corresponding point passes the standard, and when the CA value is greater than 1, it is evaluated that the corresponding point may not pass the standard, DD and Difference denote a depth difference, and DTA and Distance denote a distance to agreement.

DDTolerance and DTATolerance are respectively predetermined value as threshold limit values of the depth difference and the distance to agreement. In FIG. 15, (f) to (h) are verification results respectively in cases where the DDTolerance and DTATolerance are 1 mm, 2 mm, and 3 mm. The point shown in the drawing denotes a point that may not pass the standard.

Figure 16:
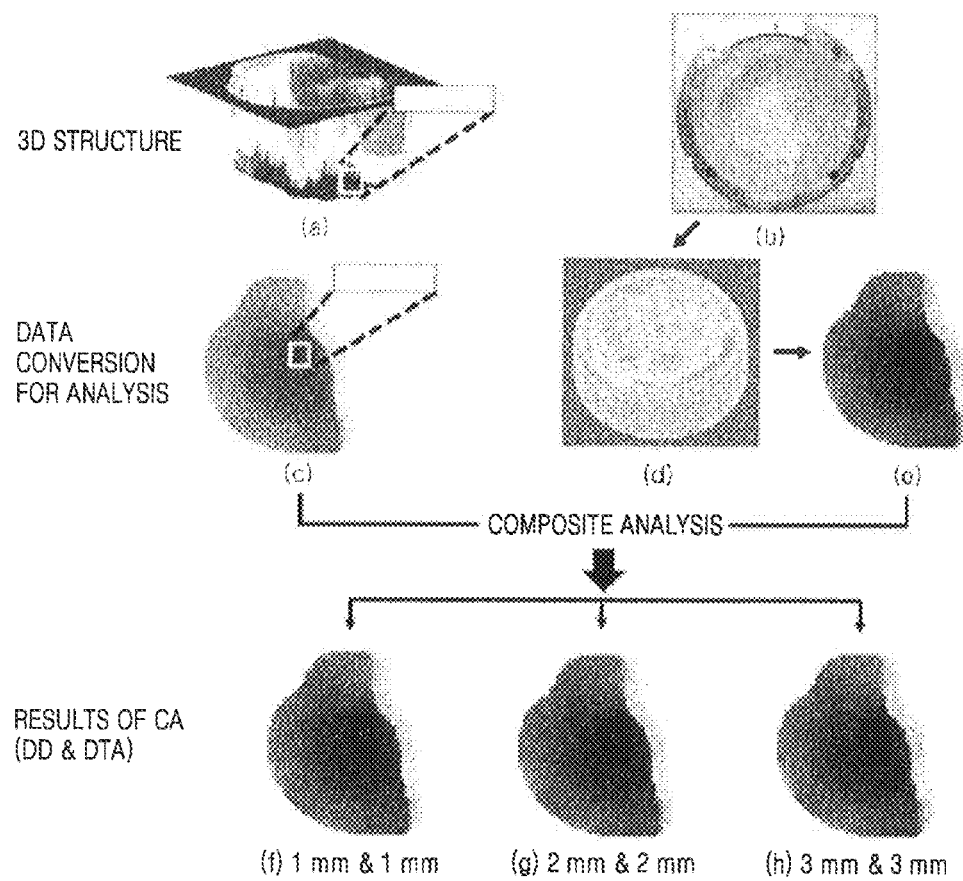
FIG. 16 is a diagram showing a result of experimentally verifying the radiation beam intensity modulator to be verified.

FIG. 16 is a diagram showing a result of experimentally verifying the verification target radiation beam intensity modulator, while varying the verification target radiation beam intensity modulator. Likewise, a point shown in FIG. 16 denotes a point that may not pass the standard.

In one embodiment, the modulator verification unit 1225 may verify the verification target radiation beam intensity modulator based on the number of pass/number of total points. For example, in a case where the number of pass/number of total points does not exceed a threshold, the verification target radiation beam intensity modulator may be verified as defective.

In one embodiment, the modulator verification unit 1225 may verify the verification target radiation beam intensity modulator based on a reference pass rate of an area that is designated as an important area. For example, based on the are input from the user as the important are, the modulator verification unit 1225 may verify the verification target radiation beam intensity modulator as defective, in a case where the number of pass/number of total points of designated area does not exceed a threshold.

In one embodiment, after the verification target radiation beam intensity modulator and the original radiation beam intensity modulator are matched, the modulator verification unit 1225 may measure a distance between the reference points (e.g., the center points, the beam isocenters, or well-known certain reference points) of the both radiation beam intensity modulators to evaluate whether there is a systematic shift caused by the apparatus for manufacturing the radiation beam intensity modulator.

In one embodiment, the modulator verification unit 1225 may calculate an error distance and direction based on the distance difference and direction between the reference points of the two radiation beam intensity modulators, and may provide information for correcting the shift of the apparatus for manufacturing the radiation beam intensity modulator.

In another embodiment, after matching the verification target radiation beam intensity modulator and the original radiation beam intensity modulator, the modulator matching unit 1224 may evaluate whether there is a systematic shift caused by the apparatus for manufacturing the radiation beam intensity modulator, and may provide information for correcting the shift of the apparatus for manufacturing the radiation beam intensity modulator by calculating the shift distance and direction.

The second controller 1226 performs the verification processes by controlling processes of each of the data receiver 1221, the original modulator structure information receiver 1222, the modulator structure reconstruction unit 1223, the modulator matching unit 1224, and the modulator verification unit 1225.

FIG. 17 is a flowchart illustrating a method of verifying a radiation beam intensity modulator according to an embodiment of the present invention.

Referring to FIG. 17, the scanner 1210 is calibrated before performing the verification procedure by using the radiation beam intensity modulator verification system 140 (S1702). For example, an object, a structure of which is already known, is scanned by the scanner 1210, and a scanning result is compared with the object to calibrate the scanner 1210.

The scanner 1210 scans the radiation beam intensity modulator 1219 manufactured by the radiation beam intensity modulator manufacturing system (hereinafter, verification target radiation beam intensity modulator) to obtain an image of the verification target radiation beam intensity modulator 1219 (81704), and generates 3D structure information of the verification target radiation beam intensity modulator 1219 based on the image. That is, the scanner 1210 may reconstruct the 3D structure of the verification target radiation beam intensity modulator 1219 as depth information. Depths of the points in the verification target radiation beam intensity modulator 1219 may be calculated by using the above equations 1 and 2, as described above.

The verification system 1220 receives the original radiation beam intensity modulator structure information from the radiotherapy treatment planning system 110 or the radiation beam intensity modulator modeling system 120 (S1712), and extracts the thickness information of the original radiation beam intensity modulator from the information (S1714). The verification system 1220 may reconstruct the extracted thickness information to the structure of the original radiation beam intensity modulator (S1716).

The verification system 1220 generates a thickness matrix of the verification target radiation beam intensity modulator and a thickness matrix of the original radiation beam intensity modulator based on the 3D structure information of the verification target radiation beam intensity modulator 1219 and the thickness information of the original radiation beam intensity modulator (S1720).

When the thickness matrixes of the two radiation beam intensity modulators are generated, the verification system 1220 matches the two radiation beam intensity modulators based on the thickness information so that the difference between the thickness matrixes of the two radiation beam intensity modulators is minimum (S1730). The process of matching the two radiation beam intensity modulators is described above with reference to equation 3.

After matching the two radiation beam intensity modulators, the verification system 1220 evaluates whether the depth difference between the matched radiation beam intensity modulators passes the standard at each point (S1740), and verifies the verification target radiation beam intensity modulator (S1750). For example, the verification system 1220 verifies the verification target radiation beam intensity modulator by evaluating whether the depth difference passes the standard through the DD analysis or the CA. The analysis method may be set by the user. In one embodiment, when the verification method is set as the DD analysis, the verification system 1220 verifies the verification target radiation beam intensity modulator by evaluating whether the difference in depths of the matched radiation beam intensity modulators passes a predetermined standard at each point. In another embodiment, when the verification method is set as the CA, the verification system 1220 performs the CA at each point whether each point passes the standard to verify the verification target radiation beam intensity modulator. The process of evaluating whether the depth difference between the matched radiation beam intensity modulators passes the standard through the CA is described above with reference to equation 4.

The verification system 1220 may verify the verification target radiation beam intensity modulator based on the number of pass/number of total points or the reference pass rate of the area designated as an important area.

The system and method described with reference to FIGS. 1 to 17 may be implemented in the form of a computer-readable storage medium including computer-executable instructions, such as computer-executable applications or modules.

The computer-readable storage medium may be any available medium that may be accessed by a computer, and includes volatile and non-volatile media and removable and non-removable media. Also, the computer-readable medium may include both a computer storage medium and a communication medium. The computer storage medium may include volatile and non-volatile media and removable and non-removable media that are implemented using any method or technology for storing information, such as computer-readable instructions, a data structure, a module, or other types of data. The communication medium typically includes computer-readable instructions, a data structure, a program module, or other data of modulated data signal such as carrier waves, or other transmission mechanisms, and includes an arbitrary information transfer medium.

The term "module" may refer to hardware capable of performing a function and operation based on the name of each component described herein, a computer program code capable of performing a specific function and operation, or an electronic storage medium (e.g., processor) on which computer program code capable of performing a specific function and operation has been installed.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A method of manufacturing a radiation beam intensity modulator, the method comprising:
obtaining, by a processor coupled to a memory storing instructions, dose modulation information expressed as a density matrix or three-dimensional (3D) structure information provided from a radiotherapy treatment planning system;

obtaining, by the processor, design condition information of a radiation beam intensity modulator provided from the radiotherapy treatment planning system;

generating, by the processor, a radiation beam intensity modulator structure based on the design condition information of the radiation beam intensity modulator and the dose modulation information expressed as the density matrix or the 3D structure information;

adjusting, by the processor, the radiation beam intensity modulator structure by comparing at least one of an actual manufacturing condition and a treatment condition with the design condition information of the radiation beam intensity modulator; and manufacturing, by the processor, the radiation beam intensity modulator based on the radiation beam intensity modulator structure that is adjusted, wherein the adjusting of the radiation beam intensity modulator structure comprises:

comparing design material information obtained from the design condition information with manufacturing material information obtained from actual manufacturing condition;

when degrees of radiation attenuation of the design material and the manufacturing material are equal to each other, maintaining a thickness of the radiation beam intensity modulator; and when degrees of radiation attenuation of the design material and the manufacturing material are different from each other, adjusting a thickness of the radiation beam intensity modulator according to a difference between the degrees of radiation attenuation.

2. The method of claim 1, wherein the design condition information of the radiation beam intensity modulator includes at least one of a distance between a source and the radiation beam intensity modulator, a location of a beam center axis, a location where the radiation beam intensity modulator is actually placed, and physical information of the radiation beam intensity modulator.

3. A method of manufacturing a radiation beam intensity modulator, the method comprising:

obtaining, by a processor coupled to a memory storing instructions, dose modulation information expressed as a density matrix or three-dimensional (3D) structure information provided from a radiotherapy treatment planning system;

obtaining, by the processor, design condition information of a radiation beam intensity modulator provided from the radiotherapy treatment planning system;

generating, by the processor, a radiation beam intensity modulator structure based on the design condition information of the radiation beam intensity modulator and the dose modulation information expressed as the density matrix or the 3D structure information;

adjusting, by the processor, the radiation beam intensity modulator structure by comparing at least one of an actual manufacturing condition and a treatment condition with the design condition information of the radiation beam intensity modulator; and manufacturing, by the processor, the radiation beam intensity modulator based on the radiation beam intensity modulator structure that is adjusted, wherein the adjusting of the radiation beam intensity modulator structure comprises:

comparing distance information between a source and the radiation beam intensity modulator in design obtained from the design condition information with distance information between a source and the radiation beam intensity modulator during treatment obtained from the actual treatment condition;

when the distance information between the source and the radiation beam intensity modulator in the design and during the treatment is constant, maintaining a size of the radiation beam intensity modulator; and when the distance information between the source and the radiation beam intensity modulator in the design and during the treatment is different, adjusting the size of the radiation beam intensity modulator according to a difference between the distance information.

4. The method of claim 1, wherein the manufacturing of the radiation beam intensity modulator is performed by using a 3D printer.

5. The method of claim 4, wherein the manufacturing of the radiation beam intensity modulator comprises:

converting information of the adjusted radiation beam intensity modulator structure into information from which the 3D printer is capable of manufacturing the radiation beam intensity modulator; and when the information of the radiation beam intensity modulator structure is partially lost during the conversion, correcting a lost part.

6. An apparatus for manufacturing a radiation beam intensity modulator, the apparatus comprising:

a memory storing instructions; and a processor coupled to the memory storing instructions configured to:

design a radiation beam intensity modulator according to a radiotherapy treatment plan;

model the radiation beam intensity modulator based on information about the radiation beam intensity modulator; and manufacture the radiation beam intensity modulator based on the radiation beam intensity modulator, wherein the modeling the radiation beam intensity modulator comprises:

obtaining dose modulation information expressed as a density matrix or 3D structure information and obtaining design condition information of the radiation beam intensity modulator;

generating a radiation beam intensity modulator structure based on the design condition information of the radiation beam intensity modulator and the dose modulation information expressed as the density matrix or the 3D structure information; and adjusting the radiation beam intensity modulator structure by comparing at least one of an actual manufacturing condition and a treatment condition with the design condition information of the radiation beam intensity modulator, wherein the adjusting the radiation beam intensity modulator structure comprises:

comparing design material information obtained from the design condition information with manufacturing material information obtained from actual manufacturing condition, when degrees of radiation attenuation of the design material and the manufacturing material are equal to each other, a thickness of the radiation beam intensity modulator is maintained, and when degrees of radiation attenuation of the design material and the manufacturing material are different from each other, a thickness of the radiation beam intensity modulator is adjusted according to a difference between the degrees of radiation attenuation.

7. An apparatus for manufacturing a radiation beam intensity modulator, the apparatus comprising:
a memory storing instructions; and
a processor coupled to the memory storing instructions, configured to:
design a radiation beam intensity modulator according to a radiotherapy treatment plan;
model the radiation beam intensity modulator based on information about the radiation beam intensity modulator; and
manufacture the radiation beam intensity modulator based on the radiation beam intensity modulator,
wherein the modeling the radiation beam intensity modulator comprises:
obtaining dose modulation information expressed as a density matrix or 3D structure information and obtaining design condition information of the radiation beam intensity modulator;
generating a radiation beam intensity modulator structure based on the design condition information of the radiation beam intensity modulator and the dose modulation information expressed as the density matrix or the 3D structure information; and
adjusting the radiation beam intensity modulator structure by comparing at least one of an actual manufacturing condition and a treatment condition with the design condition information of the radiation beam intensity modulator,
wherein the adjusting the radiation beam intensity modulator structure comprises:
comparing distance information between a source and the radiation beam intensity modulator in design obtained from the design condition information with distance information between a source and the radiation beam intensity modulator during treatment obtained from the actual treatment condition,
when the distance information between the source and the radiation beam intensity modulator in the design and during the treatment is constant, a size of the radiation beam intensity modulator is maintained, and
when the distance information between the source and the radiation beam intensity modulator in the design and during the treatment is different, the size of the radiation beam intensity modulator is adjusted according to a difference between the distance information.

8. The apparatus of claim 6, wherein the radiation beam intensity modulator modelling system further comprises an output interface configured to convert information of the adjusted radiation beam intensity modulator structure into information from which the 3D printer is capable of manufacturing the radiation beam intensity modulator.

9. The apparatus of claim 8, wherein the output interface, when the information of the radiation beam intensity modulator structure is partially lost during the conversion, corrects a lost part.

10. The method of claim 3, wherein the manufacturing of the radiation beam intensity modulator is performed by using a 3D printer.

11. The method of claim 10, wherein the manufacturing of the radiation beam intensity modulator comprises:
converting information of the adjusted radiation beam intensity modulator structure into information from which the 3D printer is capable of manufacturing the radiation beam intensity modulator; and
when the information of the radiation beam intensity modulator structure is partially lost during the conversion, correcting a lost part.

12. The apparatus of claim 7, wherein the radiation beam intensity modulator modelling system further comprises an output interface configured to convert information of the adjusted radiation beam intensity modulator structure into information from which the 3D printer is capable of manufacturing the radiation beam intensity modulator.

13. The apparatus of claim 12, wherein the output interface, when the information of the radiation beam intensity modulator structure is partially lost during the conversion, corrects a lost part.

14. The method of claim 3, wherein the design condition information of the radiation beam intensity modulator includes at least one of a distance between a source and the radiation beam intensity modulator, a location of a beam center axis, a location where the radiation beam intensity modulator is actually placed, and physical information of the radiation beam intensity modulator.

* * * * *